(12) United States Patent
Powell et al.

(10) Patent No.: US 8,449,542 B2
(45) Date of Patent: May 28, 2013

(54) IMPLANT ASSEMBLY DEVICE

(75) Inventors: Sean Powell, West Chester, PA (US);
Dipan Patel, Glen Mills, PA (US)

(73) Assignee: Synthes USA, LLC, West Chester, PA (US)

( * ) Notice: Subject to any disclaimer, the term of this patent is extended or adjusted under 35 U.S.C. 154(b) by 841 days.

(21) Appl. No.: 11/389,640

(22) Filed: Mar. 24, 2006

(65) Prior Publication Data
US 2006/0167463 A1    Jul. 27, 2006

Related U.S. Application Data

(63) Continuation of application No. 10/860,425, filed on Jun. 2, 2004, now Pat. No. 7,033,365.

(51) Int. Cl.
*A61B 17/56* (2006.01)

(52) U.S. Cl.
USPC .......................................................... 606/56

(58) Field of Classification Search
USPC ............... 606/99, 62, 64, 65, 67, 301, 89, 96, 606/98, 104; 623/20.35, 20.36, 23.15, 23.23, 623/23.27; 81/436, 451; D08/82, 83
See application file for complete search history.

(56) References Cited

U.S. PATENT DOCUMENTS

| | | | |
|---|---|---|---|
| D54,142 S | 11/1919 | Sommer | |
| 2,222,517 A | 11/1940 | Price | |
| 2,329,398 A | 9/1943 | Duffy | |
| D233,406 S | 10/1974 | Whiteford | |
| 3,892,232 A | 7/1975 | Neufeld | |
| D248,922 S | 8/1978 | Osak, Jr. | |
| 4,950,270 A | 8/1990 | Bowman et al. | |
| 5,100,404 A | 3/1992 | Hayes | |
| 5,176,681 A | 1/1993 | Lawes et al. | |
| 5,295,991 A | 3/1994 | Frigg | |
| 5,352,228 A | 10/1994 | Kummer et al. | |
| 5,354,299 A | 10/1994 | Coleman | |
| 5,458,604 A | 10/1995 | Schmieding | |
| 5,478,341 A | 12/1995 | Cook et al. | |
| 5,665,086 A | 9/1997 | Itoman et al. | |
| 5,961,516 A | 10/1999 | Graf | |
| 6,106,528 A | 8/2000 | Durham et al. | |
| 6,168,595 B1 | 1/2001 | Durham et al. | |
| 6,183,477 B1 | 2/2001 | Pepper | |
| 6,321,626 B1 | 11/2001 | Liu | |
| 6,375,658 B1 | 4/2002 | Hangody et al. | |
| 6,565,573 B1 | 5/2003 | Ferrante et al. | |
| 6,799,480 B1 | 10/2004 | Walsh et al. | |
| 2002/0032447 A1 | 3/2002 | Weikel et al. | |
| 2002/0169453 A1 | 11/2002 | Berger | |
| 2003/0120277 A1 | 6/2003 | Berger | |

FOREIGN PATENT DOCUMENTS

JP        9164151        6/1997

*Primary Examiner* — Eduardo C Robert
*Assistant Examiner* — David Comstock
(74) *Attorney, Agent, or Firm* — Fay, Kaplun & Marcin, LLP

(57) ABSTRACT

An implant assembly device for use in inserting a bone fixation implant includes: (a) a handle portion for manipulation by a user and (b) a shaft having a proximal end and a distal end. The proximal end of the shaft connected to the handle portion. The distal end of the shaft includes a screw engaging portion configured and adapted to engage and rotate a connecting screw. The device also includes (c) an elongated rod extended through the shaft from a proximal end to a distal end thereof The proximal end of the elongated rod is non-movably coupled to the shaft and the distal end of the elongated rod extending distally past of the distal end of the shaft. The elongated rod is configured and dimensioned to simultaneously pass through an interior portion of, and support, an implant insertion handle, the connecting screw and the bone fixation implant.

21 Claims, 2 Drawing Sheets

IMPLANT ASSEMBLY DEVICE

RELATED APPLICATION DATA

The present application is a continuation of U.S. patent application Ser. No. 10/860,425, filed Jun. 2, 2004 now U.S. Pat. No. 7,033,365.

FIELD OF THE INVENTION

This invention relates generally to systems for the internal fixation of bone fractures, and particularly, to equipment associated with the insertion of intramedullary fracture fixation devices such as those used in the treatment of long bone fractures, such as for example fractures of the femur, tibia, humerus, etc.

BACKGROUND OF THE INVENTION

Skeletal fractures are common injuries. These fractures are typically debilitating and often require the patient to undergo surgery. Depending on the severity of the fracture, the orthopedic surgeon has several options for treatment, ranging from simple fracture reducing implants to complete prosthetic replacements. However, even when the treatment of the fracture does not call for a complicated procedure such as complete replacement, the proper setting of a fractured bone can still pose substantial challenges to even the most skilled orthopedic surgeon.

The difficulties that a surgeon has to deal with when reducing a fracture are well known. These difficulties include dealing with the shape and positioning of the bones or bone fragments when aligning the fracture and the accompanying complications regarding the proper placement of an orthopedic implant for supporting and holding the fracture in proper alignment until it heals. This latter problem of implant alignment still remains as one of the challenges facing an orthopedic surgeon in fracture surgery.

Fractures of long bones, such as the femur, are often treated with the use of an intramedullary rod ("IM rod") inserted into the medullary canal of the affected bone. An IM rod, as is well known in the art, generally comprises an elongated rod along with associated cross-members such as screws, tacks or nails, including nails having helical blades. The IM rod typically includes various transverse holes to allow for the placement of the cross-members through the IM rod and into bone tissue in order to stabilize and hold together the fragmented bone segments. For example, in the treatment of fractures in the area of the neck and/or head of the femur, a lag screw or nail (with or without helical blades) can be inserted through the proximal portion of the IM rod, across the fracture, and then into the femoral head. For more distal shaft type fractures, locking screws, bolts or nails can be placed through the IM rod and into bone tissue at appropriate locations in order to provide fixation of the bone fragments.

Implanting IM rods generally involves the insertion of the rod into the medullary canal through a point located at the end of the bone. An osteotomy is made to create an entry site and a flexible reamer is utilized to carry out the reaming of the medullary canal while conforming to its basic anatomy. Once a suitable hole has been prepared, the IM rod is inserted through the entry site and into the medullary canal. However, the size and shape of the IM rod can make its insertion into the medullary canal difficult. As the IM rod may be smooth and may have a narrow diameter, the surgeon may not be able to achieve a tight grip on the rod in surgery. Furthermore, a large amount of force may be needed to push the rod into the medullary canal and the rod may also need to be rotated along its axis or otherwise maneuvered to assist in insertion, which can all make insertion difficult. In addition, the location of the individual holes of the rod must be identified in order to place cross-members through the rod while it is in place within the medullary canal.

A variety of insertion systems have been developed in order to facilitate orthopedic implant placement in bone fracture surgery. The use of such insertion systems have assisted orthopedic surgeons in aligning and implanting fixation implants to insure the proper healing of the fracture. For example, implant insertion handles are commonly used to align and hold the IM rod as it is inserted into the marrow canal of a fractured bone, and to connect to the other implant insertion instruments, such as an aiming arm. The handle member is a curved body which may have a bore located at a first end of the handle for coupling to a fixation implant and may have a plurality of bores located at a second end of the handle. The implant insertion handle provides the surgeon with a large grip that allows the application of a large amount of force to the IM rod, allows the rod to be easily manipulated or twisted, and can be utilized as an alignment reference for cross-members that must be inserted into the bone and through the IM rod.

However, while these implant insertion handles are useful in helping to insert an IM rod, their use requires a certain amount of preparation in the operating room prior to the insertion of the IM rod. Once an appropriately sized IM rod has been selected by the surgeon, the insertion handle must be properly aligned with an alignment indicator on the proximal end of the IM rod and while the components are being held in position, a connecting screw must be inserted through the handle and into the IM rod. The connecting screw is then tightened with a screwdriver or other suitable device while the components are being held in position.

Because the various components to be connected together can be somewhat unwieldy, oftentimes the surgeon or operating room technician will have difficulty aligning and holding the components together prior to tightening the connecting screw. As described above, attaching the handle to the IM rod requires that multiple pieces be held precisely in position at the same time that a tool is used to tighten the connecting screw. The difficulties inherent in assembling these components can result in the device being dropped on the floor, thereby affecting the sterility of the instruments. In addition, components may move out of alignment while the connecting screw is being tightened, resulting in the handle being out of alignment with the IM rod. This can result in an improperly placed intramedullary rod or the inability to locate transverse openings for the insertion of cross-members through the IM rod.

SUMMARY OF THE INVENTION

A preferred embodiment of an implant assembly device is disclosed comprising a handle for manipulation by a user, a shaft having a first end and a second end, and an elongated rod extending from the second end of the shaft. The first end of the shaft is connected to the handle and the second end of the shaft comprises a screw engaging portion to engage and rotate a connecting screw. Also disclosed is a preferred method of assembling an intramedullary rod and an intramedullary rod insertion handle, comprising the steps of providing an intramedullary rod, providing an intramedullary rod insertion handle, providing an implant assembly device comprising a shaft having a first end and a second end, and an elongated rod extending from the second end of the shaft, wherein the second end of the shaft has a screw engaging portion to rotate a screw, placing a cannulated connecting screw onto the rod of the implant assembly device, placing an intramedullary rod insertion handle onto the rod of the implant assembly device, placing the intramedullary rod onto the rod of the implant assembly device, aligning the intramedullary rod and the insertion handle to a desired configuration, and twisting the implant assembly device so that the connecting screw connects the insertion handle to the intramedullary rod. Also disclosed is an embodiment of an intramedullary rod insertion kit comprising an intramedullary rod insertion handle having first and second ends, the first end of the insertion handle adapted to removably connect to an intramedullary rod, the intramedullary rod insertion handle having a bore at its first end, a connecting screw configured to extend through the bore of the insertion handle and engage an intramedullary rod, the connecting screw being cannulated and having a rotation tool engagement portion, an implant assembly device comprising a shaft having first and second ends, and an elongated rod extending from the second end of the shaft, wherein the second end of the shaft is configured to engage and rotate the rotation tool engagement portion of the connecting screw and the elongated rod is sized and configured to extend through the connecting screw and the insertion handle and into the intramedullary rod.

The implant assembly device of the present invention allows a surgeon or operating room technician to attach insertion instruments to an IM rod with a reduced risk of dropping the instruments or improperly aligning the instruments with each other. The implant assembly device is designed to be used with intramedullary rods or other orthopedic fracture fixation devices, and their associated implant insertion instruments such as those shown in pending U.S. application Ser. No. 10/269,976, the disclosure of which is expressly incorporated herein by reference.

The implant insertion instruments may comprise a handle member for implantation of a first fixation implant (or a first portion of an implant), an arm member for guiding of a second fixation implant (or a second portion of the implant) into bone, a sleeve member for protection of soft tissue and for translational and rotational control of the second fixation implant, a nut member for engaging the sleeve member, and a drive shaft with coupling member for attachment to the second fixation implant and for driving the second fixation implant through the arm member and sleeve member into the fractured bone. The implant insertion instruments may also include a striking member to aid the surgeon in inserting the first fixation implant into the fractured bone. A measuring device that reduces measuring errors made by a user and a measuring device that determines implant length, diameter, and angle of insertion may also be included. These implant insertion instruments may have a bore running though them (known as a cannulation) that allows them to be placed over a guide wire or a push rod during insertion.

The implant assembly device of the present invention allows the surgeon or operating room technician to easily and securely attach an implant insertion instrument to an intramedullary rod by holding the various related components aligned and in position on a pushrod while a connecting screw is locked into position. The device can be held with one hand while the various components are placed one by one into their proper position onto the pushrod of the device, leaving the other hand free to manipulate the other components. When all of the pieces are in position, an integrated screw engaging portion of the rod fits into the connecting screw and allows the user to tighten the screw simply by turning the handle to complete the assembly. The implant assembly device is then removed from the device and the intramedullary rod is ready for insertion into the fractured bone.

An implant assembly device of the present invention may comprise a handle, a shaft with a first end and a second end, and an elongated rod extending from the shaft. The first end of the shaft is connected to the handle and the second end of the shaft is configured to engage the head of a connecting screw. In one embodiment of the implant assembly device, the handle is spherical and is provided with a plurality of surface grooves. In another embodiment of the implant assembly device, the handle is spherical and is provided with a grippable surface and the second end of the shaft has a hexagonal, square, Torx™, spline, or keyed shape for engaging the head of a connecting screw. The handle may be composed of AL 6061-T6 aluminum alloy, and may also be provided with a plurality of gripping inserts. The shaft may be composed of Grade 431 stainless steel, and is preferably about 40 mm long, although the length may be longer or shorter as necessary. The elongated rod extending from the shaft may be between 50 mm and 400 mm long and may be composed of Grade 316 stainless steel.

An alternative embodiment of the implant assembly device may have a handle integrally formed with a shaft that extends from the handle, a screw-engaging portion formed on the end of the shaft; and an elongated rod extending from the shaft. The shaft may be removably attached to the handle and the rod may be removably attached to the shaft. Optionally, the rod and shaft may be integrally formed with a screw engaging portion located between the ends of the integral rod/shaft. The elongated integral rod/shaft may also be removably attached to the handle. The handle may be spherical and may be provided with a plurality of surface grooves, and the screw-engaging portion of the shaft may have a hexagonal, square, Torx™, spline, or keyed shape.

The implant assembly device may be used to assemble an intramedullary rod and a handle by: choosing an appropriately sized intramedullary rod; placing a cannulated connecting screw onto a rod of an implant assembly device; sliding the cannulated connecting screw along the rod so that the connecting screw engages a screw engaging portion of a shaft extending from a handle of the implant assembly device; placing an intramedullary rod insertion handle onto the rod of the implant assembly device; sliding the insertion handle along the rod so that the connecting screw engages the insertion handle, placing the intramedullary rod onto the rod of the implant assembly device; sliding the intramedullary rod along the rod to engage the insertion handle; aligning the intramedullary rod and the insertion handle to a desired configuration; and twisting the handle of the implant assembly device to tighten the connecting screw so that the insertion handle is secured to the intramedullary rod.

BRIEF DESCRIPTION OF THE DRAWINGS

The disclosed figures are for purposes of description and may illustrate preferred features of the implant assembly device which may be optional, and which further may be combined or used singularly. These figures are intended to be illustrative only and in no way serve to limit the scope of the invention. The present invention is limited only by the claims.

DETAILED DESCRIPTION OF THE INVENTION

Figure 3:
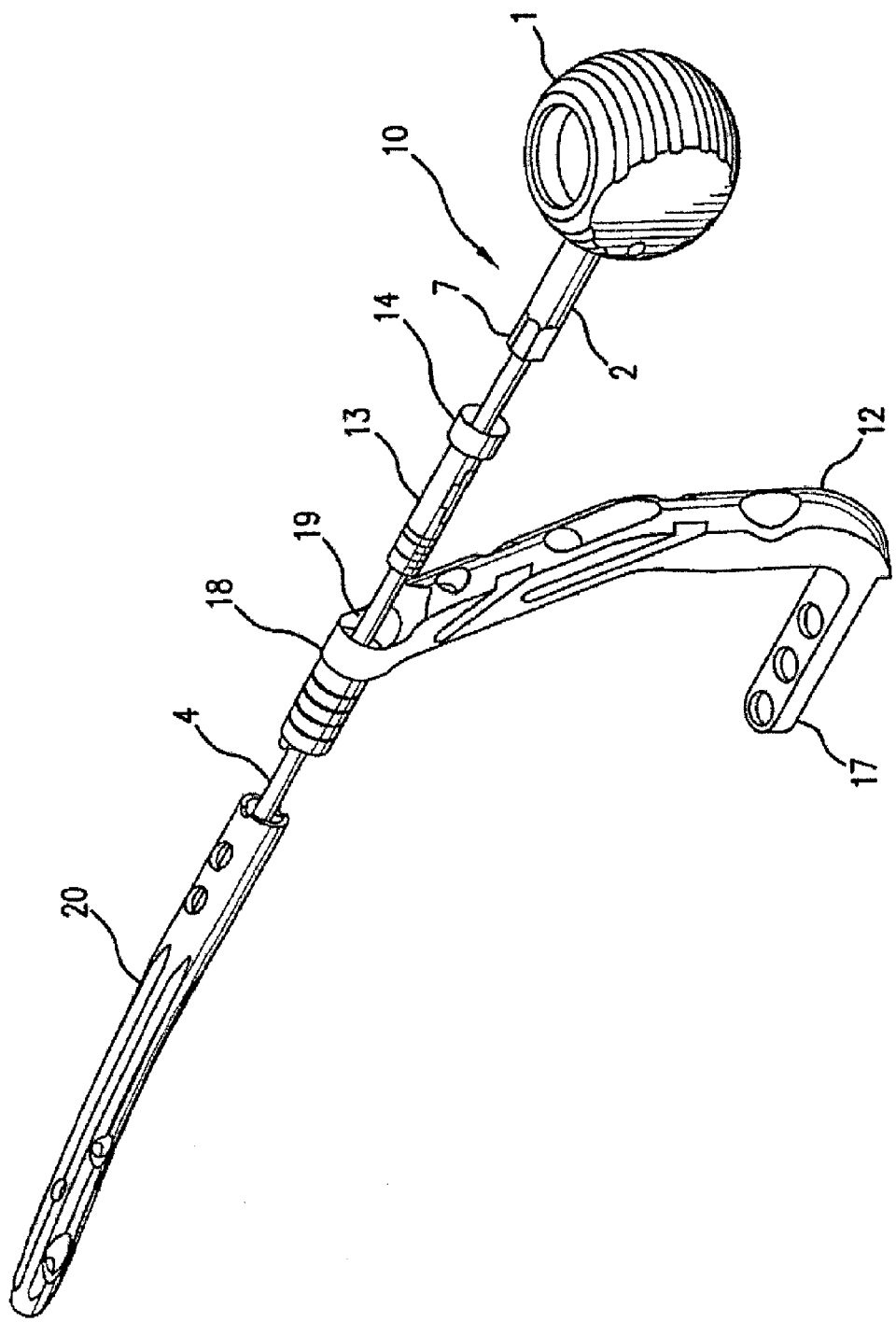
FIG. 3 is a perspective view of an IM rod, an insertion handle and a connection screw in a partially assembled configuration, mounted on the implant assembly device.

FIG. 3 shows the preferred embodiment of the implant assembly device 10, along with an IM rod 20 and various components that may be associated with the insertion of an IM rod. FIG. 3 shows a connecting screw 13 and an insertion handle 12 in a partially assembled configuration as each is placed on the device 10 prior to being locked into position on the IM rod 20.

Figure 1:
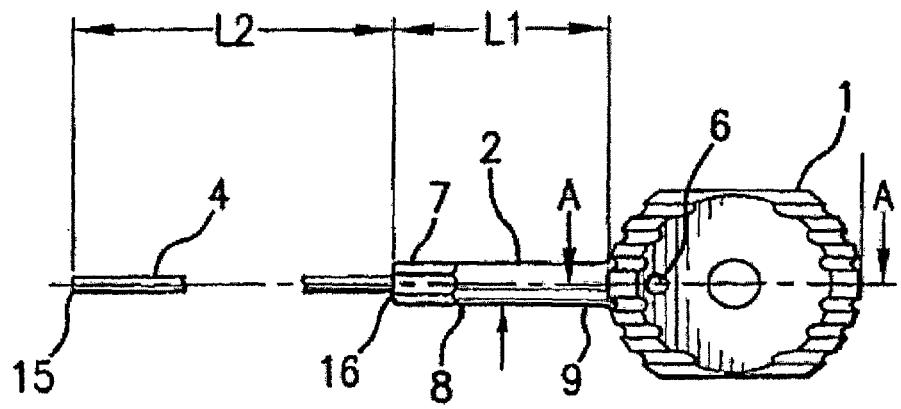
FIG. 1 is a plan view of an exemplary embodiment of the implant assembly device of the present invention.
Figure 2:
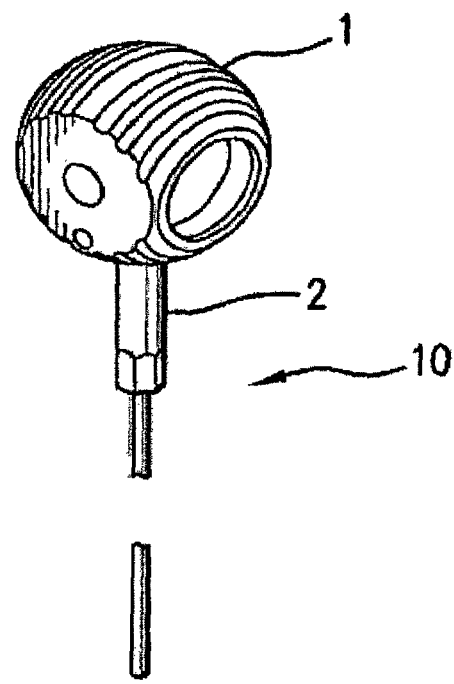
FIG. 2 is a perspective view of the exemplary embodiment of the implant assembly device of the present invention.

As illustrated in FIGS. 1 and 2, handle 1 is preferably connected to a shaft 2 that extends from the body of handle 1. The handle 1 preferably is of an appropriate size and shape to be easily gripped by a user and to allow the user to apply a rotational force to the device. While the handle is shown in a generally spherical configuration, the handle may also be of any shape that preferably allows the user to grip the device. The handle may be provided with grooves or other form of surface irregularities or texturing to improve the gripping qualities of the handle. The handle may alternatively be provided with a surface treatment, covering, or inserts which likewise improve the gripping qualities of the handle. The handle may be composed of an aluminum alloy such as AL 6061-T6, but other suitable materials, both metallic and non-metallic, may be used. The handle may also be substantially hollow, with or without an opening to the exterior.

To securely hold shaft 2 within the handle 1, a pin 6 or other appropriate mechanism preferably extends through the handle 1 and into or against shaft 2. Securing the shaft 2 to the handle 1 can also be accomplished by other means known to those of skill in the art. For example, shaft 2 may be provided with a threaded surface which engages a similarly threaded bore present in the handle 1, the shaft 2 may be press fit into handle 1 or otherwise welded, brazed or cemented together. In another embodiment, the shaft 2 is integrally formed with the handle 1, thereby providing a single piece shaft/handle unit.

The shaft 2 is preferably composed of an appropriate metal or metal alloy, such as Grade 431 stainless steel, although other materials which exhibit the properties desired by a user could conceivably be implemented as well. Shaft 2 has first 8 and second 9 ends, and a length L1. Length L1 may be from 10 mm to 100 mm, and most preferably is 40 mm. Shaft 2 may have a circular cross-section and may have a diameter that is sized as required to provide a screw engaging portion 7 appropriate to engage the screw to be used. Most preferably, the diameter of the shaft 2 is approximately 9 mm. Understandably, larger or smaller diameter shafts 2 may be used as required. In addition, while shaft 2 has been described as having a circular cross-section, it may be provided in other shapes as well. The first end 8 of shaft 2 preferably has a screw engaging portion 7 preferably in the shape of a hexagonal section which is designed to engage the corresponding preferably hexagonal inset found in the head 14 of a connecting screw 13. The second end 9 of the shaft 2 is inserted into the handle 1 of the implant assembly device 10. Other sizes, shapes or configurations of the engaging portion 7 of the shaft 2 can also be used as appropriate to engage the head 14 of a connecting screw 13. For example, the end of shaft 2 may have a square, Torx™, spline, star, or keyed shape for engaging the head 14 of a connecting screw 13 and applying the desired rotation to the screw. Shaft 2 may also be solid or cannulated as desired.

Preferably, an about 3.0 mm diameter rod 4 extends from shaft 2. The rod 4 is similar to the guide rods commonly used in orthopedic surgery to align and position implants inserted into bones. However, the rod 4 may be of a smaller or larger diameter, or solid or hollow, as required, without detracting from the operation of the device. In addition, while the rod has been described as having a diameter with a circular cross-section, one skilled in the art will appreciate that other shapes and configurations may be used for rod 4 such as, for example, a square cross-section, an "I" cross-section, a "C" or "T" cross-section, etc. The rod 4 is preferably made of Grade 316 stainless steel, however, other metals, metal alloys, or other types of materials which exhibit the appropriate properties may also be used.

The rod 4 has first 15 and second 16 ends, and a length L2. The rod 4 preferably is sufficiently stiff to support the various components placed upon it, while at the same time exhibit a certain amount of flexibility to accommodate the bends or curvatures of the IM rod or insertion components. The length L2 of rod 4 is preferably about 250 mm to about 350 mm, and more preferably about 320 mm long, although the length of the rod 4 may be longer or shorter as necessary to meet the demands of the implant instruments. For example, rods of approximately 50 mm in length may be used to assemble insertion handles with solid IM rods with a limited length bore at its proximal end.

The rod 4 is preferably connected to the shaft 2 by brazing before the shaft is inserted into the handle. In another embodiment, the rod 4 is securely held by the shaft 2 by a pin extending through the handle 1 and shaft 2, into or against the rod 4. It is contemplated that the rod 4 can be held in the handle 1 by other means known to those of skill in the art. For example, the rod 4 may be press-fit into the shaft 2 and held only by the frictional fit within the shaft 2. The rod 4 may also be threaded or otherwise prepared to interconnect with the shaft 2. In another embodiment, the rod 4 may be configured to be removably connected to the shaft 2, thereby allowing the use of different length rods as required under the circumstances. Alternatively, the rod and shaft can be formed as an integral piece, with the screw engaging portion 7 being located between the ends 9, 15 of the integral rod/shaft.

During the course of surgery to fix a fracture, the surgeon may determine the appropriate length and diameter IM rod to be used based upon the physical characteristics of the patient. To connect the chosen IM rod to the insertion handle 12, the surgeon or operating room technician then slides a cannulated connecting screw 13 onto the rod 4 of the implant assembly device 10. The connecting screw 13 preferably has a bore forming the cannulation, the bore preferably being about 1 mm to about 10 mm, and most preferably greater than about 3 mm. The connecting screw 13 preferably has threads at its first end to engage threads formed in the more of the intramedullary rod, and a rotation tool engaging portion preferably in the form of a shaped recess at its second end for engagement with the screw engaging portion 7 of the implant assembly device 10. An insertion handle 12 with a first end 18, a second end 17 and a bore 19 is then placed over the rod 4, followed by the IM rod 20 being placed over the rod 4. Other components to be attached to the IM rod 20 and the insertion handle 12, such as those described above, can also be placed on the rod 4 of the implant assembly device 10 at this time in the desired sequence. Because the various components are being supported by the rod 4, the task of the operating room technician is greatly simplified. The implant assembly device 10 can be held in one hand with a reduced chance of dropping one of the various components that are placed on the rod 4. Once all the pieces are in position, the IM rod 20 and insertion handle 12 may be carefully manipulated (i.e. rotated) about the rod 4 into proper alignment with each other. Other components can also be aligned at this time as desired. Following the alignment of the various components, the IM rod 20 and the insertion handle 12 are connected to each other by rotating the ball handle 1 to tighten the connecting screw 13. More specifically the screw engaging portion 7 of the shaft 2 engages the connecting screw 13. It is not necessary for the operating room technician to remove his hands from the assemblage to reach for an additional tool to lock the connection screw into position, but instead the handle 1 need only be rotated to tighten the cannulated connecting screw 13.

While it is apparent that the illustrative embodiments of the invention herein disclosed fulfill the objectives of the disclosed invention, it will be appreciated that numerous modifications and other embodiments may be devised by those skilled in the art. Therefore, it will be understood that the appended claims are intended to cover all such modifications and embodiments which come within the spirit and scope of the present invention.

What is claimed:

1. An implant assembly device for use in inserting a bone fixation implant comprising:
    a handle portion for manipulation by a user,
    a shaft having a proximal end and a distal end, the proximal end of the shaft connected to the handle portion and the distal end of the shaft including a screw engaging portion configured and adapted to engage and rotate a connecting screw, and
    an elongated rod extending through the shaft from a proximal end to a distal end thereof, the proximal end of the elongated rod being non-movably coupled to the shaft and the distal end of the elongated rod extending distally past the distal end of the shaft, the elongated rod configured and dimensioned to simultaneously pass through an interior portion of, and support, an implant insertion handle, the connecting screw and the bone fixation implant.

2. The implant assembly device of claim 1, wherein the handle portion is substantially spherical and is provided with a plurality of surface grooves.

3. The implant assembly device of claim 2, wherein the handle portion is composed of AL 6061-T6 aluminum alloy.

4. The implant assembly device of claim 1, wherein the screw engagement portion has a shape selected from at least one of the group consisting of a hexagon, square, star, spline, and keyed shape for engaging the head of the connecting screw.

5. The implant assembly device of claim 1, wherein the handle portion is provided with a plurality gripping inserts.

6. The implant assembly device of claim 1, wherein the shaft has a length of between about 10 mm and about 100 mm.

7. The implant assembly device of claim 6, wherein the elongated rod extending from the shaft is between about 50 mm and about 400 mm long.

8. The implant assembly device of claim 7 wherein the elongated rod has a diameter of between 1 mm and 10 mm.

9. The implant assembly device of claim 1 wherein the handle portion is integrally formed with the shaft.

10. The implant assembly device of claim 1, wherein the elongated rod is removably attached to the shaft.

11. The implant assembly device of claim 1, wherein the shaft is removably attached to the handle portion.

12. The implant assembly device of claim 1, wherein the rod is integrally formed with the shaft and the screw engaging portion is positioned between the ends of the rod and shaft.

13. The implant assembly device of claim 1 wherein the screw engaging portion is positioned about 200 mm to about 350 mm from the end of the rod.

14. An implant assembly device for use in inserting a bone fixation implant comprising:
    a handle portion for manipulation by a user,
    a shaft having a proximal end and a distal end, the proximal end of the shaft connected to the handle portion and the distal end of the shaft including a screw engaging portion configured and adapted to engage and rotate a connecting screw, and
    an elongated rod extending through the shaft from a proximal end to a distal end thereof, the proximal end of the elongated rod being non-movably coupled to the shaft and the distal end of the elongated rod extending distally past the distal end of the shaft, the elongated rod configured and dimensioned to simultaneously pass through an interior portion of, and support, an implant insertion handle, the connecting screw and the bone fixation implant,
    wherein the distal end of the elongated rod is non-threaded.

15. The implant assembly device of claim 14, wherein the handle portion is substantially spherical and is provided with a plurality of surface grooves.

16. The implant assembly device of claim 14, wherein the handle portion is integrally formed with the shaft.

17. The implant assembly device of claim 14, wherein the elongated rod is removably attached to the shaft.

18. The implant assembly device of claim 14, wherein the rod is integrally formed with the shaft.

19. A bone fixation implant insertion kit comprising:
    a bone fixation implant;
    an implant insertion handle having a first end configured and dimensioned for removable attachment to the bone fixation implant;
    a connecting screw having a first end configured and dimensioned for joining the insertion handle to the bone fixation implant; and
    an implant assembly device including
    a handle portion for manipulation by a user,
    a shaft having a proximal end and a distal end, the proximal end of the shaft connected to the handle portion and the distal end of the shaft including a screw engaging portion configured and adapted to engage and rotate the connecting screw, and
    an elongated rod extending through the shaft from a proximal end to a distal end thereof, the proximal end of the elongated rod being non-movably coupled to the shaft and the distal end of the elongated rod extending distally past the distal end of the shaft, the elongated rod configured and dimensioned to simultaneously pass through an interior portion of and support the insertion handle, the connecting screw and the bone fixation implant.

20. The bone fixation implant insertion kit of claim 19, wherein the implant insertion handle further comprises a mounting for the attachment of an aiming arm.

21. The bone fixation implant insertion kit of claim 19, wherein the elongated rod is removably attached to the shaft.

* * * * *